United States Patent
Giacca et al.

(10) Patent No.: US 11,155,818 B2
(45) Date of Patent: Oct. 26, 2021

(54) MICRORNA HSA-MIR-665 IN CARDIAC HYPERTROPHY

(71) Applicant: INTERNATIONAL CENTRE FOR GENETIC ENGINEERING AND BIOTECHNOLOGY—ICGEB, Trieste (IT)

(72) Inventors: Mauro Giacca, Trieste (IT); Luca Braga, Trieste (IT); Matteo Dal Ferro, Trieste (IT); Miguel Luis Cunha Mano, Coimbra (PT); Ana Sofia Bregieiro Eulalio, Coimbra (PT)

(73) Assignee: KING'S COLLEGE LONDON, London (GB)

( * ) Notice: Subject to any disclaimer, the term of this patent is extended or adjusted under 35 U.S.C. 154(b) by 123 days.

(21) Appl. No.: 16/493,569

(22) PCT Filed: Mar. 13, 2018

(86) PCT No.: PCT/EP2018/056230
§ 371 (c)(1),
(2) Date: Sep. 12, 2019

(87) PCT Pub. No.: WO2018/167057
PCT Pub. Date: Sep. 20, 2018

(65) Prior Publication Data
US 2021/0071175 A1    Mar. 11, 2021

(30) Foreign Application Priority Data
Mar. 14, 2017   (EP) ..................................... 17160768

(51) Int. Cl.
*C12N 15/113*     (2010.01)
*C12N 15/86*      (2006.01)
*C12Q 1/68*       (2018.01)

(52) U.S. Cl.
CPC ............ *C12N 15/113* (2013.01); *C12N 15/86* (2013.01); *C12N 2310/141* (2013.01); *C12N 2750/14143* (2013.01)

(58) Field of Classification Search
None
See application file for complete search history.

(56) References Cited

FOREIGN PATENT DOCUMENTS

| EP | 2305810 A1 | 6/2011 |
| WO | 2013093870 A1 | 6/2013 |
| WO | 2013127782 A2 | 9/2013 |

OTHER PUBLICATIONS

Jayawardena et al., "MicroRNA-mediated in vitro and in vivo Direct Reprogramming of Cardiac Fibroblasts to Cardiomyocytes" Circ Res., 2012, v 110, n 11, p. 1465-1473.
Li et al., "Identification of cardiac-related circulating microRNA profile in human chronic heart failure" Oncotarget, 2015, v 7, n 1, p. 33-45.
Brittain et al., "One generation's junk is another's treasure: The emerging role of microRNAs as therapeutic targets" J Heart Lung Transplant, 2014, v 33, n 3, p. 233-234.
Mohnle et al., "MicroRNA-665 is involved in the regulation of the expression of the cardioprotective cannabinoid receptor CB2 in patients with severe heart failure" Biochemical and Biophysical Research Communications, 2014, v 451, p. 516-521.

*Primary Examiner* — Sean McGarry
(74) *Attorney, Agent, or Firm* — Greer, Burns & Crain, Ltd.; Gregory P. Einhorn

(57) ABSTRACT

The present invention refers to human microRNA hsa-miR-665 for the treatment or prevention of heart diseases associated with cardiac hypertrophy and consequent pathological remodeling of the heart, in particular for preventing and/or treating heart failure (HF). Vectors and pharmaceutical compositions comprising said miRNA for the disclosed uses are also within the scope of the present invention.

Figure 1:
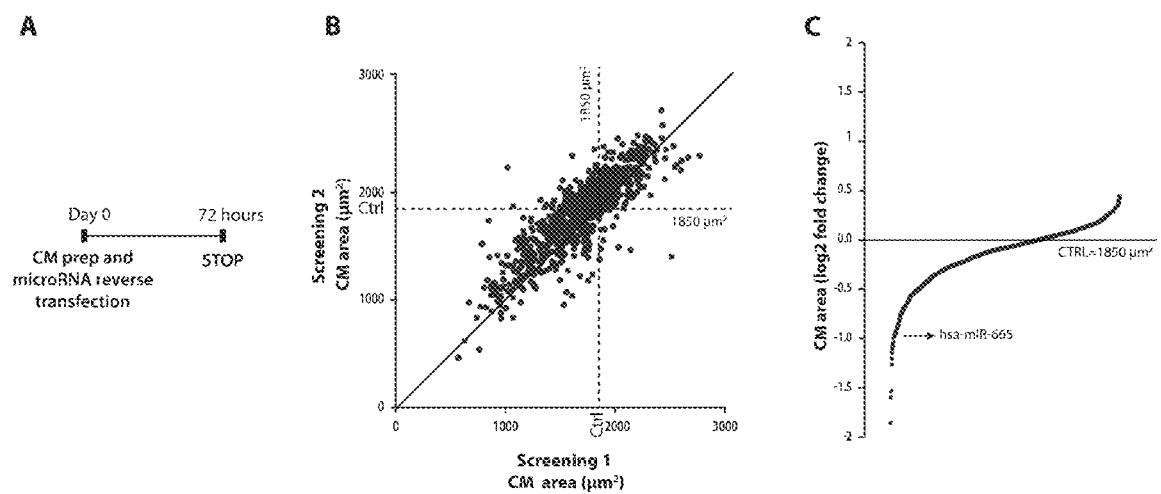

20 Claims, 5 Drawing Sheets
Specification includes a Sequence Listing.

SEQUENCE LISTING

```
<160> NUMBER OF SEQ ID NOS: 2

<210> SEQ ID NO 1
<211> LENGTH: 72
<212> TYPE: RNA
<213> ORGANISM: Homo sapiens
<220> FEATURE:
<223> OTHER INFORMATION: hsa-mir-665 Accession number MI0005563

<400> SEQUENCE: 1
ucuccucgag gggucucugc cucuacccag gacucuuuca ugaccaggag gcugaggccc       60
cucacaggcg gc                                                          72

<210> SEQ ID NO 2
<211> LENGTH: 20
<212> TYPE: RNA
<213> ORGANISM: Homo sapiens
<220> FEATURE:
<223> OTHER INFORMATION: hsa-miR-665 Mature Sequence accession number
      MIMAT0004952

<400> SEQUENCE: 2
accaggaggc ugaggcsccu                                                    20
```

MICRORNA HSA-MIR-665 IN CARDIAC HYPERTROPHY

RELATED APPLICATIONS

This application is a U.S. national phase patent application claiming benefit of priority to PCT International patent application number PCT/EP2018/056230, filed Mar. 13, 2018, which claims priority to EP Patent application no. 17160768.2, filed Mar. 14, 2017. The aforementioned applications are expressly incorporated herein by reference in its entirety and for all purposes.

The present invention relates to the fields of pharmaceuticals and biotechnology.

In particular, the present invention refers to the human microRNA hsa-miR-665 for the treatment of heart diseases associated with cardiac hypertrophy and consequent pathological remodeling of the heart, in particular for preventing and/or treating heart failure (HF).

BACKGROUND OF THE INVENTION

Despite recent advances in cardiovascular surgery and therapy, cardiovascular diseases (CVDs) are responsible of over 17 million deaths each year, corresponding to 31% of all deaths worldwide (http://www.who.int/caardiovascular_diseases/en/). The burden of CVD is no longer restricted to the high-income population, since 80% of these deaths occur in middle- and low-income countries.

Within the spectrum of CVDs, heart failure (HF) represents a final condition determined by different underlying pathological causes. The American Heart Association/American College of Cardiology guidelines define HF as a "a complex clinical syndrome that can result from any structural or functional cardiac disorder that impairs the ability of the ventricle to fill or eject blood" [1] [2]. This syndrome affects more than 26 million individuals worldwide, of whom 74% suffer at least 1 comorbidity, which is considerably worsened by HF [3].

The adult heart is a dynamic organ, capable of significant remodeling in response to different extrinsic and intrinsic stimuli. The majority of pathological stimuli first induce a phase of cardiac hypertrophy, resulting from a compensatory increase in individual cardiomyocyte size. Later, this often evolves into a form of decompensated hypertrophy, eventually determining remodeling of the LV anatomy and precipitating into overt HF (reviewed in references [4]-[5]). Compensatory hypertrophy can be determined by cardiomyocyte loss due to chronic or sudden ischemic damage (ischemic cardiomyopathy or myocardial infarction), chronic hypertension or cardiac valve disease (reviewed in [5]). The same response is also observed as the result of different genetic mutations in hereditary cardiomyopathies leading to an hypertrophic phenotype (reviewed in [5]).

Cardiomyocyte hypertrophy is also commonly associated with the development of HF with preserved left ventricle (LV) Ejection Fraction (EF), HFpEF, which now accounts for approximately 50% of the HF cases. As far as this condition is concerned, epidemiological observation suggests that prevalence of HFpEF, relative to HF with reduced EF (HFrEF, which is typically observed due to ischemic heart disease), is growing by 10% per decade, thus reaching epidemic proportions [6, 7]. This trend is sustained by the increasing rate of HFpEF-associated comorbidities (in particular, hypertension and obesity), increase in average life span of the population and better management of patients with coronary artery disease (CAD). Mortality of patients with HFpEF is close to 60% at 5 years, hospitalization rate is high and quality of life becomes severely impaired.

Currently treatments for HFrEF resulting from CAD (in particular, angiotensin aldosterone system-inhibitors, beta-blockers, LCZ696, pacemaker/device therapy) are instead largely ineffective in HFpEF patients [8]. Treatment with statin has shown relative benefit in a small clinical trial on 185 patients with HFpEF [9]; however, a working-mechanism for this drug is still missing and this result has not yet replicated in larger number of patients.

The physiology and molecular correlates of HFpEF are complex and very partially understood. The disease evolves progressively from asymptomatic to symptomatic and is variably characterized by LV hypertrophy, slow LV relaxation, LV diastolic stiffness, decreased LV systolic performance, left atrial remodeling, peripheral vascular resistance, impaired endothelial function, increased pulmonary arterial and venous resistance, neurohormonal activation and ventricular-arterial coupling [10]. While the underlying etiology of HFpEF remains unclear, there is ample consensus that two most remarkable phenotypic correlates of this condition are increased cardiomyocyte stiffness [11] and impaired cardiomyocyte contractility [12]. Ageing lengthens relaxation and increases LV stiffness by collagen accumulation and cross-linking [13], cardiomyocyte loss and reactive hypertrophy [14].

Therefore, there is still the need of a therapeutic tool for the treatment of cardiac hypertrophy and its consequences, in particular heart failure, more in particular for the treatment of the currently incurable heart failure with preserved left ventricle (LV) Ejection Fraction (EF) form (HFpEF).

Furthermore, it would be desirable to intervene in a cardiac hypertrophy condition to prevent the development of associated diseases.

MicroRNAs are evolutionarily conserved small noncoding RNAs that regulate gene expression at the post-transcriptional level, by imperfect base-pairing to complementary sequences present in the target messenger mRNA, more often in its 3'-UTR but also in the 5'UTR and coding sequence. Paring results in translation repression, mRNA degradation, or both [15]. The microRNA seed sequence, essential for the binding of the microRNA to the mRNA, is a conserved sequence, most often located at positions 2-8 from the microRNA 5'-end [16].

MicroRNAs are genome-encoded sequences generally transcribed by RNA polymerase II into primary microRNAs (pri-microRNAs). The pri-microRNAs are then sequentially processed by different cellular endonucleases to eventually generate a duplex containing two strands, of about 19-23 nucleotides. The microRNA duplex is then unwound, and the mature microRNA is incorporated into the RNA-induced silencing complex (RISC), which mediates silencing by microRNAs (reviewed in reference [17]).

The role of different microRNAs in cardiac development, hypertrophy and heart failure has been extensively investigated (reviewed in references: [18]; [19]). In particular, it was shown that microRNAs are involved in proper cardiac development. Ablation of whole microRNAs network by the knock-out of Dicer, in both the developing and adult heart, leads to severe heart failure and death [20]. Furthermore, many studies of gain- and loss-of-function have highlighted microRNA families or single microRNAs involved in pathological cardiac remodeling, raising the possibility to use these microRNAs either as biomarkers or targets for novel therapies (reviewed in references: [21] and [22]). Several microRNAs have been described to regulate specific processes in cardiac biology, including cardiomyocyte proliferation (miR-1 [23], miR-133a [24], miR-199a-3p [25]), cardiomyocyte hypertrophy (miR-208a [26], microRNA-212/132 family [27], miR-378 [28]), cardiac fibrosis (miR-29 [29], miR-21 [30], miR-378 [28]), cardiomyocytes contractility (miR-208a [26]).

Given the role of microRNAs in virtually any human disease, many of them have been considered as targets for innovative therapies and a few also as therapeutic agents themselves.

However, only a few of these potential applications have reached clinical experimentation so far, and none of these for the treatment of cardiac diseases.

Therefore, microRNAs involved in heart failure and which can be used in the treatment of heart failure and related diseases, with special reference to the currently incurable HFpEF form, are highly desired.

It has now been found a previously unknown role of the microRNA hsa-miR-665 in regulating cardiomyocyte function.

Indeed, it has been found that said microRNA effectively reduces the size of rat and mouse neonatal cardiomyocytes in pro-hypertrophic conditions.

Previous published evidence has reported that this microRNA is increased in the blood of patients with heart failure [31]. Another report indicates, on the contrary, that patients with heart failure have even lower intracardiac levels of the same microRNA [32].

However, a causative or effective role for this microRNA in the development or, even less, in the treatment of heart failure has not been shown or even suggested in the prior art.

It has now been found a previously unknown, pharmacological role of hsa-miR-665 once administered exogenously to cultured cardiomyocytes and to the heart in vivo.

In particular, it has been found that in hypertrophic conditions the said microRNA blocks and reduce cardiac hypertrophy and pathological cardiac remodeling at the same time increasing cardiac function. Also, it has been found that this microRNA specifically down-regulates the expression of genes involved in the regulation of biomechanical stress response further supporting its therapeutic use in hypertrophic conditions.

These results, obtained in well assessed and accepted animal models, allow the development of medicaments comprising hsa-miR-665 for the treatment of cardiac diseases in human subjects.

hsa-miR-665 can be used as a therapeutic option to counteract pathological hypertrophy and prevent and/or treat heart failure.

Also, said microRNA can be used to prevent and/or treat all conditions characterized by pathological cardiac hypertrophy, in particular involving increased cardiomyocyte stiffness, such as for example post-ischemic pathological hypertrophy, HFpEF and genetically-determined cardiomyopathies with an hypertrophic phenotype.

SUMMARY OF THE INVENTION

It is an object of the invention the microRNA hsa-miR-665 for the prevention and/or the treatment of cardiac pathologies characterized by cardiac hypertrophy.

In particular, said disease can be selected from the group consisting of pathological cardiac hypertrophy, heart failure with preserved ejection fraction (HFpEF), heart failure with reduced ejection fraction (HFrEF) and cardiomyopathy of genetic and non-genetic origin.

In particular, it is an object of the invention the microRNA hsa-miR-665 for the prevention and/or the treatment of heart failure, in particular when heart failure is consequent or associated to cardiac hypertrophy.

More in particular, said microRNA can be used for restoring the cardiac function after development of hypertrophy.

Also, it can be used in conditions at risk of developing cardiac hypertrophy, such as for example myocardial infarction and cardiomyopathy of ischemic or non-ischemic derivation.

A method for modulating, preventing and/or treating cardiac hypertrophy in vivo comprising the administration of hsa-miR-665 to a subject in need thereof is also within the scope of the invention.

Compositions, vectors and formulations for the administration of hsa-miR-665 for the above mentioned uses are also within the scope of the invention.

DESCRIPTION OF THE INVENTION

Definitions

Within the meaning of the present invention, for heart failure it is intended a complex clinical syndrome that can result from any structural or functional cardiac disorder that impairs the ability of the ventricle to fill or eject blood.

Within the meaning of the present invention, for cardiac hypertrophy it is intended the abnormal enlargement, or thickening, of the heart muscle, resulting from increases in cardiomyocyte size and changes in other heart muscle components, such as extracellular matrix, which results in a decrease in cardiac function.

FIGURES

FIG. 1. High-content screening for microRNAs regulating cardiomyocyte cell size. A, Screening workflow. B. Correlation between CM size across screening replicates, Spearman coefficient=0.84. Each dot represent the effect of an individual microRNA. The dotted lines indicate the average area of normal control CMs. CM area fold change over control (CTRL) following transfection with 875 microRNAs; approximately 2500 cells were analysed per microRNA/replicate. The effect of hsa-miR-665 is specifically indicated.

Figure 2:
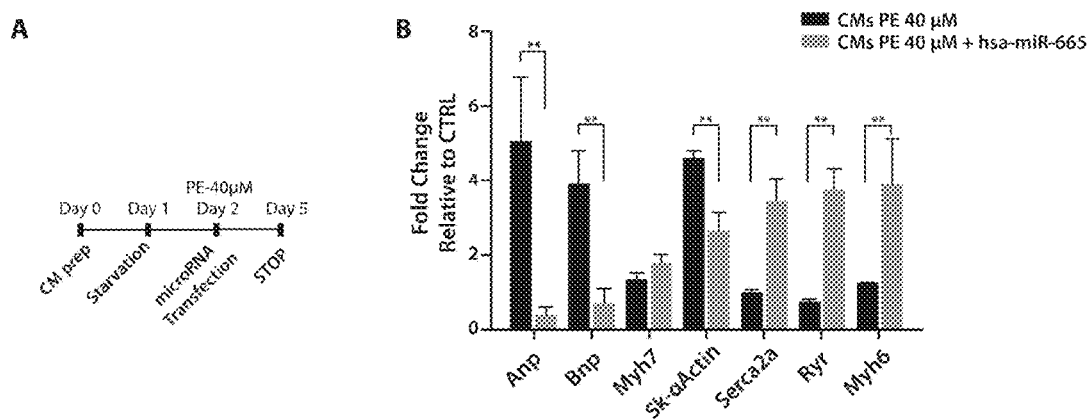

FIG. 2. Validation of hsa-miR-665 anti-hypertrophic effect in rat CMs. A, Experimental model. B. Levels of expression of the indicated genes as evaluated by qRT-PCR after treatment of rat CMs with phenylephrine PE (40 µM) or phenylephrine PE (40 µM) and transfected with hsa-miR-665. The results are mean±s.d. of at least three different experiments. **$P<0.01$ of hsa-miR-665 vs. untreated cardiomyocytes.

Figure 3:
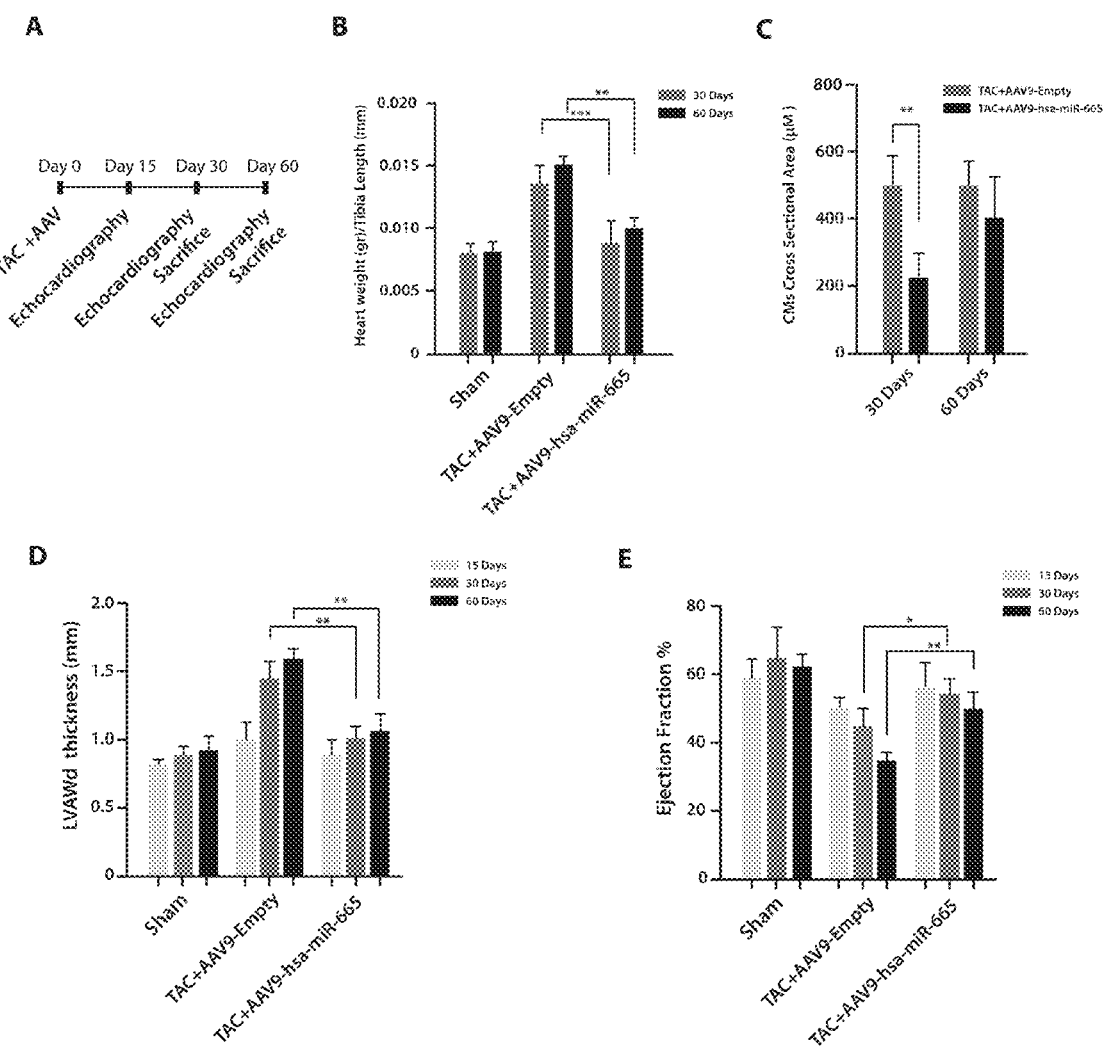

FIG. 3. Effect of overexpression of hsa-miR-665 in a TAC model of chronic pressure overload. A, Experimental model: sham surgery or thoracic aortic constriction (TAC) was performed in 10 weeks old female CD1 mice. At the same time mice (n=8), which received TAC surgery, were injected with AAV9-hsa-miR-665 or an AAV9 control (1×1011 vg/animal). Heart function was analysed by echocardiography at 15, 30 and 60 days post-TAC, and mice were sacrificed at days 30 or 60 post-TAC for histological analysis. B, Heart mass, reported as the ratio of heart weight to tibia length for sham, AAV9-Empty, AAV9-hsa-miR-665, 30 and 60 days after TAC. $P<0.01$; *$P<0.001$. C, Measurement of CM cross-sectional area after Periodic Acid-Schiff (PAS) staining of heart sections in mice with the same treatment as in panel B. D and E. Echocardiographic evaluation of LV anterior wall thickness (LVAW) during diastole and ejection fraction (EF) (panels D and E respectively) at 30, 45 and 60 days after AAV-control or AAV-miR-665 intra-cardiac injection ($1 \times 10^{11}$ vg/animal). *P<0.05; P<0.01; *P<0.001.

Figure 4:
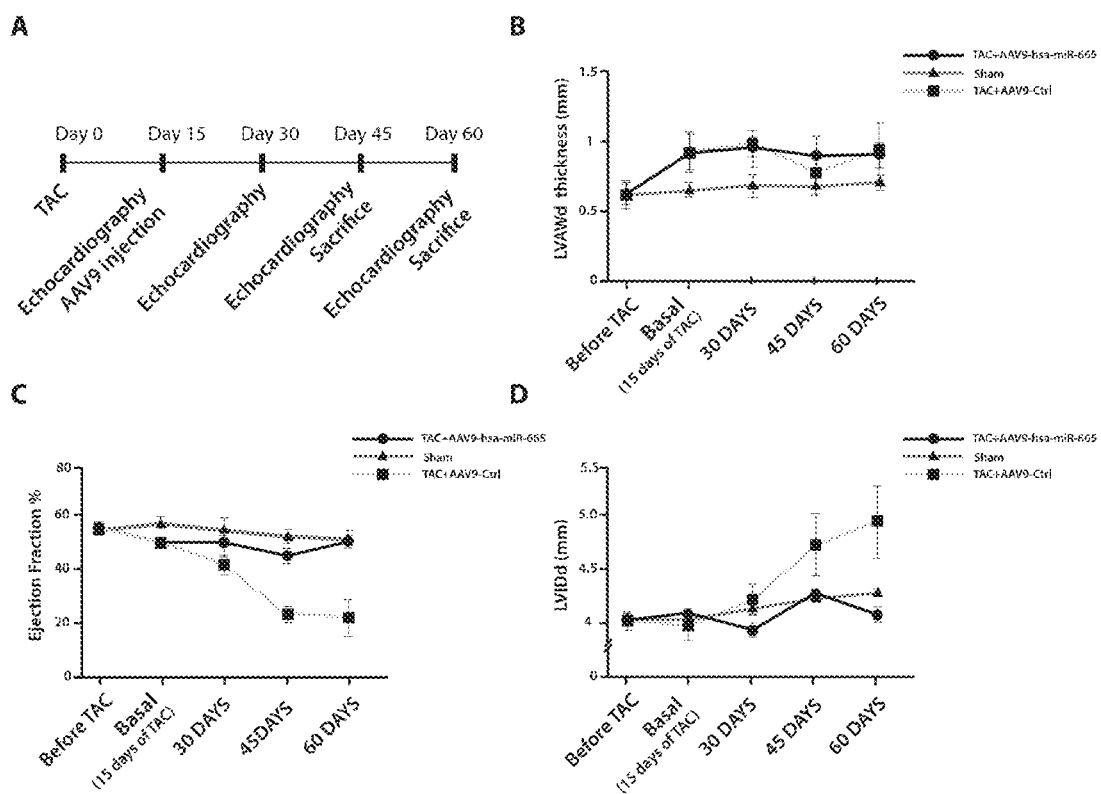

FIG. 4. Effect of overexpression of hsa-miR-665 on established hypertrophic phenotype. A, Experimental model: sham surgery or thoracic aortic constriction (TAC) was performed in 10 weeks old female CD1 mice. 15 days after TAC mice (n=8), which received TAC surgery, were injected with AAV9-hsa-miR-665 or an AAV9 control (1×1011 vg/animal), heart function was analysed by echocardiography at 30, 45 and 60 days post-TAC, and mice were sacrificed at days 45 or 60 post-TAC for histological analysis. Echocardiography measurement of LVAWd—Left Ventricle Anterior Wall thickness during Diastole (B), EF—Ejection Fraction (C), LVID—Left Ventricle Internal Diameter (D) at 30, 45 and 60 days after TAC.

Figure 5:
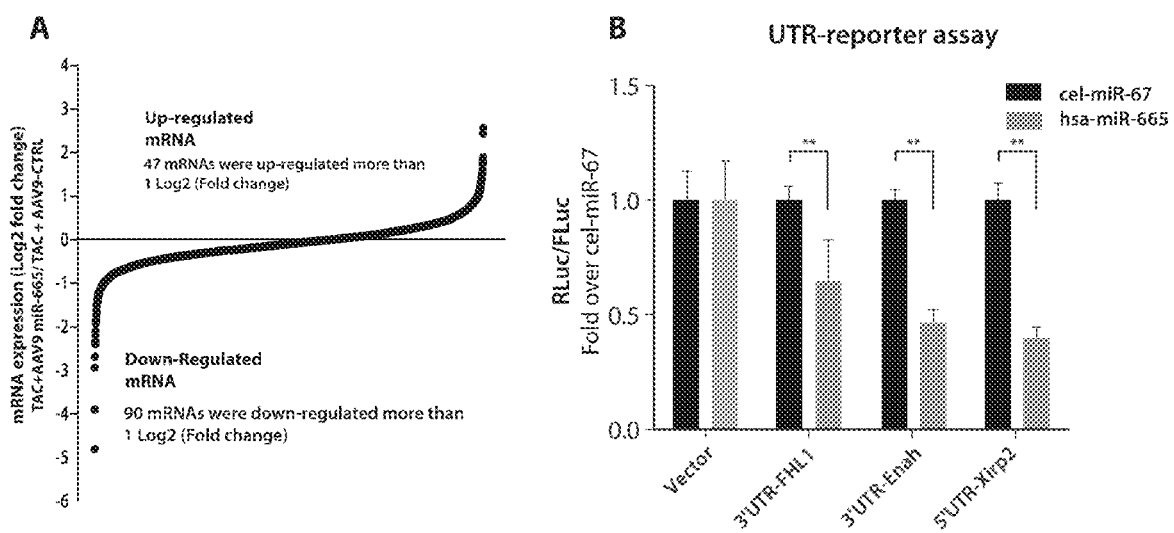

FIG. 5. hsa-miR-665 directly targets FHI1, Enah and Xirp2. A, In vivo mRNAseq of mouse samples upon hsa-miR-665 overexpression under TAC compared to control; Log2 Fold change of mRNA up/down regulated in TAC-mice injected with AAV9-hsa-miR-665 (n=3) over TAC-mice injected with AAV9-Ctrl (n=3). B, 3'-UTR luciferase reporter assays performed in HeLa cells transfected with cel-miR-67 (non-targeting control) or hsa-miR-665. Results are shown for the 3'-UTRs of Fhl1, Enah and for the 5'UTRs of Xirp2, as well as for the empty vector (Vector); *Renilla* luciferase activity was normalized to that of firefly luciferase. Values are presented as mean±s.d. *p<0.05 **P<0.01

The sequence of hsa-miR-665 is available in the state of the art with the ID hsa-miR-665 (www.mirbase.org; Database Release 21; stem-loop sequence accession number MI0005563, mature sequence accession number MIMAT0004952).

In particular, hsa-miR-665 can have anyone of the following sequences:

(SEQ ID N. 1)
5'-UCUCCUCGAGGGGUCUCUGCCUCUACCCAGGACUCUUUCAUGACCAG

GAGGCUGAGGCCCCUCACAGGCGGC-3' corresponding to the accession number MI0005563;

(SEQ ID N. 2)
5'-ACCAGGAGGCUGAGGCCCCU-3' corresponding to the mature sequence accession number MIMAT0004952.

Anyone of the above sequences can be used according to the present invention.

The microRNA of the invention has been identified for the claimed use through a high-content, fluorescence-microscopy-based, high-throughput screen performed in neonatal rat cardiomyocytes (CMs) using a library of 875 microRNA mimics.

The present invention also comprises primary transcripts, precursors and mimics of hsa-miR-665 for the uses herein disclosed for hsa-miR-665. The concepts of microRNA primary transcript, precursor and mimic are well-known in the art and do not require further explanations. In particular, for microRNA mimic it is intended a RNA molecule intended to "mimic" the activity and function of the native microRNA. The use of DNA coding for hsa-miR-665 is also within the scope of the present invention. Such DNA, for example a cDNA, can be designed according to the general knowledge in the field.

It has been found that microRNA hsa-miR-665 has an anti-hypertrophic action. Indeed, it is able to reduce cardiomyocyte size.

More in particular, it has been found that hsa-miR-665 effectively reduces the size of rat and mouse neonatal cardiomyocytes under strong pro-hypertrophic conditions and negatively regulates expression of genes associated with pathological cardiac remodeling after pathological hypertrophy, such as atrial natriuretic peptide (ANP), α-skeletal actin (sk-α actin) and brain natriuretic peptide (BNP), while upregulating genes involved in normal cardiac function (Serca2a, ryanodine receptor (Ryr) and α-myosin heavy chain (Myh6). It has also been found that hsa-miR-665 blocks cardiac hypertrophy and pathological cardiac remodeling whilst increasing cardiac function, after intracardiac injection of a viral vector expressing this microRNA in a mouse model of LV pressure overload.

Therefore, said microRNA is able to prevent the pathological cardiac remodeling which may occur after pathological hypertrophy.

Furthermore, it has been found that hsa-miR-665 is able to rescue the pathological phenotype and increase life span of mice subject to pathological LV pressure overload by preventing LV dilatation and HF.

Therefore, said microRNA can be used for the treatment of cardiac hypertrophy and for the prevention of heart failure.

Finally, it has been found that, without being limited to a specific mechanism of action, hsa-miR-665 activity involves the post-transcriptional regulation of genes involved in cardiomyocyte contractility and, in particular, regulating cardiomyocyte response to pressure overload by modulating cell stiffness and elasticity, thus further consolidating the role of this microRNA in modulation of cardiac hypertrophy.

hsa-miR-665 can therefore be used in the treatment of any condition characterized by cardiac hypertrophy, in particular involving increased cardiomyocyte stiffness.

In particular, it can be used in the prevention or in the treatment of any cardiac pathology characterized by cardiac hypertrophy.

The skilled person in the field, for example a physician specialized in the cardiology field, is able to identify the pathologies characterized by cardiac hypertrophy according to the common knowledge in the field. Reference can also be made to the last edition of the Hurst's "The Heart" by Fuster and other authors, Mc Growth Hill.

Said microRNA can also be advantageously used in any condition at risk of developing cardiac hypertrophy.

Indeed, for prevention it is intended the administration of the microRNA to a subject liable or at risk to develop a condition of cardiac hypertrophy and therefore a related cardiac disease due, for example, to genetic predisposition, environment conditions or the presence of some conditions or pathologies, such as hypertension.

For example, it can be used in conditions characterized by cardiomyocyte loss due to chronic or sudden ischemic damage, such as ischemic cardiomyopathy and myocardial infarction, in chronic hypertension, in cardiac valve diseases, in hereditary cardiomyopathies leading to an hypertrophic phenotype and in cardiomyopathies of unknown etiology, in particular characterized by increased diastolic dysfunction.

Thanks to its activity on cardiomyocyte size and stiffness, the hsa-miR-665 can in particular be advantageously used for the prevention or the treatment of heart failure with preserved left ventricle ejection fraction (HFpEF).

Said disease which can be prevented or treated by the microRNA of the invention is preferably selected from the group consisting of pathological cardiac hypertrophy, in particular post-ischemic pathological hypertrophy, cardiomyopathy of genetic and non-genetic origin, myocardial infarction, cardiomyopathy of ischemic or non-ischemic derivation, myocardial ischemia and heart failure, including heart failure with preserved ejection fraction (HFpEF) and heart failure with reduced ejection fraction (HFrEF).

The use of hsa-miR-665 in gene therapy is also a preferred embodiment of the invention.

For gene therapy it is intended the therapeutic delivery of nucleic acid polymers into a patient's cells as a drug to treat a disease. According to the present invention, hsa-miR-665 can be delivered to cells of a subject in need thereof, for example a subject affected by or at risk of developing cardiac hypertrophy or heart failure or any of the above mentioned diseases, in order to treat such diseases.

A further object of the present invention is an RNA stretch comprising the said microRNA. The notion of RNA stretch as a continuous tract of RNA is commonly known in the field. Said RNA stretch can be obtained in vitro through cell-free transcription methods, produced synthetically or expressed in the cells upon transfer of the relative DNA coding sequence, or introduced or expressed in the cells by administration of a plasmid, a viral or other type of vector.

The present invention provides said RNA stretch for use as a medicament for prevention and/or treatment of cardiac hypertrophy and of any of the above mentioned diseases.

In embodiments of the present invention, the microRNA hsa-miR-665 can be administered to a subject as a medicament by conventional methods.

Conveniently, said medicament is in the form of a preparation for parenteral, intracoronary, intravenous or intracardiac administration, but other forms are equally suitable for carrying out the present invention. The person skilled in the art will decide the effective time of administration, depending on the patient's conditions, degree of severity of the disease, response of the patient and any other clinical parameter within the general knowledge of this matter.

Another object of the present invention is a pharmaceutical composition comprising microRNA hsa-miR-665 as active ingredient for the prevention and/or treatment of cardiac hypertrophy and of any associated condition, in particular heart failure.

The pharmaceutical composition according to the invention contains at least one of the following: synthetic RNA corresponding to the microRNA of the present invention or its primary transcript or precursor, DNA coding for said microRNA, DNA coding for a primary transcript or precursor for said RNA such as the microRNA is produced inside the cells containing this DNA.

The microRNA (or primary transcript or precursor) of the present invention or the corresponding coding DNA can be administered together with lipidic molecules such as cationic lipids, or peptides, or in the context of polymeric scaffolds, which can facilitate their delivery, according to the art.

When the miRNA is administered using as a vector a lipidic molecule, such as a liposome, the sequence of the miRNA is preferably SEQ ID N.2 (accession number MIMAT0004952).

Another method to administer such microRNA or its corresponding DNA is by means of a suitable vector known for the administration of RNA or DNA.

A preferred vector is the adeno-associated vector (AAV) of any capsid serotype, either natural (such as, but not restricted to, AAV1, AAV2, AAV8, AAV9) or artificial, a well-known viral vector for administration of DNA in vivo [33].

When the miRNA is administered using as a vector a viral vector, the sequence of the miRNA is preferably SEQ ID N.1 (accession number MI0005563).

A vector for use according to the present invention comprising at least the microRNA hsa-miR-665 and/or a DNA coding for at least said microRNA and/or a DNA coding for at least a primary transcript or a precursor or a mimic of said microRNA, or a combination thereof is also an object of the invention.

All these methods and formulations to administer a synthetic RNA corresponding to the microRNA of the present invention, DNA coding for said microRNA, DNA coding for a primary transcript or precursor for said RNA such as the microRNA is produced inside the cells containing this DNA, are conventional and well known in the art and do not need further explanations.

In particular, the skilled person knows how to choose the suitable administration mode and vector, for example for human administration, according to the general knowledge in the field.

Intracardiac injection and systemic injection are preferred administration routes. However, the skilled person in the art can decide to administer microRNAs by means of any conventional pharmaceutical composition. Reference can be made to Remington's Pharmaceutical Sciences, last edition.

The administration regime, dosage and posology will be determined by the physician according to his experience, the disease to be treated and the patient's conditions.

According to the administration route chosen, the compositions will be in solid or liquid form, suitable for oral, parenteral, intravenous or intra-arterial administration.

The compositions according to the present invention contain, along with the active ingredient, at least one pharmaceutically acceptable vehicle or excipient. These may be particularly useful formulation coadjuvants, e.g. solubilising agents, dispersing agents, suspension agents, and emulsifying agents.

Average quantities of the active agent may vary and in particular should be based upon the recommendations and prescription of a qualified physician.

The following examples further illustrate the invention.

EXAMPLES

Example 1

High-Content, Fluorescence-Microscopy-Based, High-Throughput Screen Identifies microRNAs Able to Modify Cardiomyocytes Size.

A high-content, fluorescence-microscopy-based, high-throughput screen was performed in neonatal rat cardiomyocytes (CMs) using a library of 875 microRNA mimics (988 mature microRNAs, 875 unique sequences, miRBase release 13.0 (2009), http://mirbase.org). Cultures of neonatal rat ventricular CMs were reverse transfected with the library of microRNA mimics. After 72 h, the cells were stained for sarcomeric α-actinin to specifically measure CM size and number. (Experimental scheme in FIG. 1, panel A). The screening was performed in duplicate; the replicates showed very good reproducibility (Spearman coefficient 0.84; FIG. 1B). FIG. 1 panel C reports the effect of each microRNA on CMs cell size expressed as fold change over mock transfected CMs. On average, approximately 2500 cells were analysed per experimental condition and replicate.

We found 11 microRNAs able to reduce CM cell size more than 1 Log2 fold over control (CMs transfected with miR-cel67); hsa-miR-665 was among the most effective anti-hypertrophic microRNAs.

Example 2

Validation of the Screening Hits

Based on the screening results, we decided to validate and characterize the effect of the selected top microRNAs under both anti-hypertrophic and pro-hypertrophic conditions, with the specific purpose to assess the capacity of each microRNA to counteract or induce the hypertrophic phenotype. First, we investigated the effect of each microRNA on the expression of a set of genes previously associated with either pathological hypertrophy (foetal cardiac gene program: atrial natriuretic peptide (ANP), brain natriuretic peptide (BNP), β-myosin heavy chain (MYH7) and α-skeletal actin (sk-α actin) [4] or physiological hypertrophy (Serca2a, α-myosin heavy chain (MYH6) and ryanodine receptor (RYR) [4]. In particular, to examine the effect of microRNAs able to decrease CM cell size, we stimulated these cells with phenylephrine (PE), a known pro-hypertrophic stimulus, and simultaneously transfected them with individual microRNAs. Total RNA was extracted 72 h after transfection and analysed by qRT-PCR using TaqMan probes specific for the investigated subset of genes (experimental scheme FIG. 2, panel A). The pure effect of PE (40 µM) on rat CMs cultured in 0.1% FBS was evaluated after 72 h of treatment, in the absence of microRNAs, by qRT-PCR. PE strongly up-regulated the subset of genes typical of the foetal cardiac gene program (ANP, BNP and sk-α actin) and significantly increased CM size compared to control (FIG. 2, panel B).

hsa-miR-665 was able to revert the signature of pathological hypertrophy induced by PE by reducing the levels of ANP and BNP, simultaneously upregulating Serca2a, RyR and MYH6, all known markers of good contractility (FIG. 2, panel B) [34, 35].

Example 3

Hsa-miR-665 Counteracts the Onset of Hypertrophy and Preserves Cardiac Function after Transverse Aortic Constriction in Mice To evaluate the anti-hypertrophic effect of hsa-miR-665 in vivo, we investigated whether this microRNA was able to prevent hypertrophy in a transverse aortic constriction (TAC) model of chronic cardiac pressure overload. Eight-week-old CD1 mice were subjected to TAC or sham surgery and, simultaneously, injected in the LV anterior wall (LVAW) with adeno-associated virus (MV) serotype 9 (AAV9) vectors expressing hsa-miR-665 or a control vector ($1 \times 10^{11}$ vg/animal; n=8 per group; FIG. 3, panel A). Our previous experience indicates that this procedure results in efficient myocardial transduction and month-long expression of the transgene [25].

As reported in FIG. 3 panel B, overexpression of hsa-miR-665 successfully counteracted, at both 30 and 60 days, the hypertrophic remodelling of the heart and maintained heart mass at physiological levels (30 days after TAC, heart mass (gr) normalized on tibia length (mm) was 0.09±0.020; compared with 0.013±0.019 for the animals that received the control vector, P<0.001; at 60 day after TAC, 0.010±0.0006 for AAV9-miR-665 injected animals and 0.015±0.0008 for the animals that received the control vector P<0.01).

Periodic Acid-Shiff (PAS) staining of the heart sections of the treated and control mice revealed a marked reduction in cardiomyocyte cross sectional area at 30 days after TAC (242.26±76.020 µm2 for AAV9-miR-665 injected animals, compared to 487.26±104.27 µm2 for the animals that received the control vector, P<0.001). (FIG. 3, panel C).

As evaluated by echocardiography at 15, 30 and 60 days after TAC, LV anterior wall thickness (LVAW) in diastole was significantly decreased in the hsa-miR-665-treated mice compared to controls at both 30 and 60 days. At 30 days after TAC, AAV9-miR-665 injected animals had a LVAW thickness-d of 1.01±0.05 mm, compared to 1.36±0.65 mm for the animals that received the control vector, P<0.01, this effect was maintained up to 60 day after TAC, 1.02±0.15 mm for AAV9-miR-665 and 1.44±0.8 mm for control treated animals; P<0.01 (FIG. 3, panel D).

Remarkably, at 30 and 60 days after TAC, left ventricular ejection fraction (LVEF) was also markedly preserved in constricted mice treated with AAV9-miR-665 compared to control animals (FIG. 3, panel E) (30 days after TAC LVEF of AAV9-miR-665 injected animals was 56.5±5.4 compared to 42.54±5.90% in control treated animals, P<0.05; at 60 days after TAC LVEF of AAV9-miR-665 injected animals was 51.3±5.8 compared to 34.82±0.77% in control treated animals, P<0.01).

Taken together, these results indicate that the over-expression of hsa-miR-665 after aortic banding exerts a beneficial effect in reducing cardiac hypertrophy and preserving cardiac function in a chronic cardiac overload model, consistent with the effect that this microRNA showed in vitro in reducing pathological cardiomyocyte hypertrophy.

Example 4

Hsa-miR-665 Delays Cardiac Dilatation and Dysfunction Development in Hypertrophic Hearts Focusing on a possible translational application of these results, next we decided to verify whether hsa-miR-665 could rescue pathological hypertrophy development and return to a normal cardiac phenotype.

In this rescue experiment, mice were injected in the LVAW, 2 weeks after TAC surgery, with AAV9-hsa-miR-665 or an AAV9 control ($1 \times 10^{11}$ vg/animal; 10 weeks old female CD1 mice, n=8 per group). Animals followed at day 30, 45 and 60 (experimental scheme in FIG. 4, panel A). While no significant rescue of the mild hypertrophic phenotype was observed during follow up (at day 15/30 post AAV injection—45 and 60 post TAC, LVAW-d thickness: 0.88±1.13/0.91±0.08 mm for AAV9-miR-665 treated animals, compared to control with 0.8±0.11/0.96±0.33 mm), LVID-d and EF were strongly maintained in normal ranges in treated animals in respect to controls. (LVEF at final time point: 57.5%±5.60 vs 28.4%±15 in treated and control animals respectively, p<0.001; LVID-d at final time: 4.05±0.16 mm 4.8±0.69 mm in treated and control animals respectively, p<0.001) (FIG. 4 panel B, C and D).

Collectively, these results indicate that hsa-miR-665 exerts a profound beneficial effect in preserving cardiac function after aortic-constriction-induced pressure overload. These results appear to coincide with the capacity of this microRNA to prevent cardiomyocyte hypertrophy both ex vivo and in vivo.

Example 5

Hsa-miR-665 Targets Four and Half Lim Domain 1 (FHL1) and Promotes LV Compliance To identify the relevant targets of hsa-miR-665, we assessed global transcriptome changes in the heart by RNAdeep-sequencing after TAC and transduction with hsa-miR-665 or AAV-control. This analysis identified 90 down-regulated transcripts (FPKM≥20, threshold set to 2-fold down-regulation) and 47 up-regulated mRNAs (FPKM≥20, threshold set to 2-fold up-regulation) (FIG. 5, panel A). Then, we looked for the down-regulated transcripts that were functionally linked to sarcomeric I-band mechano-transduction and myofibrillar remodelling.

This approach identified three sarcomeric proteins (namely Enah, Fhl1 and Xirp2) that were shown by UTR-luciferase reporter assay to be direct targets of hsa-miR-665 (FIG. 5, panel B).

All these transcripts encode for proteins that localize in the proximity of the intercalated discs (IDs). Here they integrate and transduce multiple mechanical stimuli, thereby promoting cardiac hypertrophic remodelling both at a transcriptional and a structural level [36-39]. Moreover, it has been shown by Sheikh F. et al ([40]) that FHL1 binds the N2B region of titin, which is the spring-like domain responsible for myofibrillar passive tension during diastolic function [41] [42]. In fact, the heart of FHL1−/− mice presents decreased myocardial stiffness, and increased systolic function as well as a blunted hypertrophic phenotype after TAC [40].

These results indicate that the anti-hypertrophic effect of hsa-miR-665 is exerted, at least in part, through the down-regulation of genes known to mediate the biomechanical stress response in cardiomyocytes.

REFERENCES

1. Hunt, S. A., C. American College of, and G. American Heart Association Task Force on Practice, *ACC/AHA 2005 guideline update for the diagnosis and management of chronic heart failure in the adult: a report of the American College of Cardiology/American Heart Association Task Force on Practice Guidelines (Writing Committee to Update the 2001 Guidelines for the Evaluation and Management of Heart Failure)*. J Am Coll Cardiol, 2005. 46(6): p. e1-82.
2. Jessup, M., et al., *2009 focused update: ACCF/AHA Guidelines for the Diagnosis and Management of Heart Failure in Adults: a report of the American College of Cardiology Foundation/American Heart Association Task Force on Practice Guidelines: developed in collaboration with the International Society for Heart and Lung Transplantation*. Circulation, 2009. 119(14): p. 1977-2016.
3. Ambrosy, A. P., et al., *The global health and economic burden of hospitalizations for heart failure: lessons learned from hospitalized heart failure registries*. J Am Coll Cardiol, 2014. 63(12): p. 1123-33.
4. Bernardo, B. C., et al., *Molecular distinction between physiological and pathological cardiac hypertrophy: experimental findings and therapeutic strategies*. Pharmacol Ther, 2010. 128(1): p. 191-227.
5. Frey, N. and E. N. Olson, *Cardiac hypertrophy: the good, the bad, and the ugly*. Annu Rev Physiol, 2003. 65: p. 45-79.
6. Kitzman, D. W., et al., *Pathophysiological characterization of isolated diastolic heart failure in comparison to systolic heart failure*. JAMA, 2002. 288(17): p. 2144-50.
7. Bursi, F., et al., *Systolic and diastolic heart failure in the community*. JAMA, 2006. 296(18): p. 2209-16.
8. Reddy, Y. N. and B. A. Borlaug, *Heart Failure With Preserved Ejection Fraction*. Curr Probl Cardiol, 2016. 41(4): p. 145-88.
9. Fukuta, H., et al., *Statin therapy may be associated with lower mortality in patients with diastolic heart failure: a preliminary report*. Circulation, 2005. 112(3): p. 357-63.
10. Gladden, J. D., W. A. Linke, and M. M. Redfield, *Heart failure with preserved ejection fraction*. Pflugers Arch, 2014. 466(6): p. 1037-53.
11. Bhuiyan, T. and M. S. Maurer, *Heart Failure with Preserved Ejection Fraction: Persistent Diagnosis, Therapeutic Enigma*. Curr Cardiovasc Risk Rep, 2011. 5(5): p. 440-449.
12. Ponikowski, P., et al., *2016 ESC Guidelines for the diagnosis and treatment of acute and chronic heart failure: The Task Force for the diagnosis and treatment of acute and chronic heart failure of the European Society of Cardiology (ESC) Developed with the special contribution of the Heart Failure Association (HFA) of the ESC*. Eur Heart J, 2016. 37(27): p. 2129-200.
13. Hwang, S. J., V. Melenovsky, and B. A. Borlaug, *Implications of coronary artery disease in heart failure with preserved ejection fraction*. J Am Coll Cardiol, 2014. 63(25 Pt A): p. 2817-27.
14. Chung, C. S., et al., *Titin based viscosity in ventricular physiology: an integrative investigation of PEVK-actin interactions*. J Mol Cell Cardiol, 2011. 51(3): p. 428-34.
15. Eulalio, A., E. Huntzinger, and E. Izaurralde, *Getting to the root of miRNA-mediated gene silencing*. Cell, 2008. 132(1): p. 9-14.
16. Filipowicz, W., S. N. Bhattacharyya, and N. Sonenberg, *Mechanisms of post-transcriptional regulation by microRNAs: are the answers in sight?* Nat Rev Genet, 2008. 9(2): p. 102-14.
17. Ghildiyal, M. and P. D. Zamore, *Small silencing RNAs: an expanding universe*. Nat Rev Genet, 2009. 10(2): p. 94-108.
18. van Rooij, E. and E. N. Olson, *MicroRNA therapeutics for cardiovascular disease: opportunities and obstacles*. Nat Rev Drug Discov, 2012. 11(11): p. 860-72.
19. Porrello, E. R., *microRNAs in cardiac development and regeneration*. Clin Sci (Lond), 2013. 125(4): p. 151-66.
20. Hata, A., *Functions of microRNAs in cardiovascular biology and disease*. Annu Rev Physiol, 2013. 75: p. 69-93.
21. Creemers, E. E., A. J. Tijsen, and Y. M. Pinto, *Circulating microRNAs: novel biomarkers and extracellular communicators in cardiovascular disease?* Circ Res, 2012. 110(3): p. 483-95.
22. Bernardo, B. C., et al., *miRNA therapeutics: a new class of drugs with potential therapeutic applications in the heart*. Future Med Chem, 2015. 7(13): p. 1771-92.
23. Zhao, Y., et al., *Dysregulation of cardiogenesis, cardiac conduction, and cell cycle in mice lacking miRNA-1-2*. Cell, 2007. 129(2): p. 303-17.
24. Liu, N., et al., *microRNA-133a regulates cardiomyocyte proliferation and suppresses smooth muscle gene expression in the heart*. Genes Dev, 2008. 22(23): p. 3242-54.
25. Eulalio, A., et al., *Functional screening identifies miRNAs inducing cardiac regeneration*. Nature, 2012. 492 (7429): p. 376-81.
26. van Rooij, E., et al., *Control of stress-dependent cardiac growth and gene expression by a microRNA*. Science, 2007. 316(5824): p. 575-9.
27. Ucar, A., et al., *The miRNA-212/132 family regulates both cardiac hypertrophy and cardiomyocyte autophagy*. Nat Commun, 2012. 3: p. 1078.
28. Nagalingam, R. S., et al., *A cardiac-enriched microRNA, miR-378, blocks cardiac hypertrophy by targeting Ras signaling*. J Biol Chem, 2013. 288(16): p. 11216-32.

29. van Rooij, E., et al., *Dysregulation of microRNAs after myocardial infarction reveals a role of miR-29 in cardiac fibrosis.* Proc Natl Acad Sci USA, 2008. 105(35): p. 13027-32.

30. Thum, T., et al., *MicroRNA-21 contributes to myocardial disease by stimulating MAP kinase signalling in fibroblasts.* Nature, 2008. 456(7224): p. 980-4.

31. Li, H., et al., *Identification of cardiac-related circulating microRNA profile in human chronic heart failure.* Oncotarget, 2016. 7(1): p. 33-45.

32. Mohnle, P., et al., *MicroRNA-665 is involved in the regulation of the expression of the cardioprotective cannabinoid receptor CB2 in patients with severe heart failure.* Biochem Biophys Res Commun, 2014. 451(4): p. 516-21.

33. Mingozzi, F. and K. A. High, *Therapeutic in vivo gene transfer for genetic disease using AAV: progress and challenges.* Nat Rev Genet, 2011. 12(5): p. 341-55.

34. Garciarena, C. D., et al., *Endurance training in the spontaneously hypertensive rat: conversion of pathological into physiological cardiac hypertrophy.* Hypertension, 2009. 53(4): p. 708-14.

35. Iemitsu, M., et al., *Physiological and pathological cardiac hypertrophy induce different molecular phenotypes in the rat.* Am J Physiol Regul Integr Comp Physiol, 2001. 281(6): p. R2029-36.

36. Raskin, A., et al., *A novel mechanism involving four-and-a-half LIM domain protein-1 and extracellular signal-regulated kinase-2 regulates titin phosphorylation and mechanics.* J Biol Chem, 2012. 287(35): p. 29273-84.

37. Kebir, S., et al., *Sarcomeric lesions and remodeling proximal to intercalated disks in overload-induced cardiac hypertrophy.* Exp Cell Res, 2016. 348(1): p. 95-105.

38. Belmonte, S. L., et al., *Cardiac overexpression of Mammalian enabled (Mena) exacerbates heart failure in mice.* Am J Physiol Heart Circ Physiol, 2013. 305(6): p. H875-84.

39. van der Ven, P. F., et al., *Unusual splicing events result in distinct Xin isoforms that associate differentially with filamin c and Mena/VASP.* Exp Cell Res, 2006. 312(11): p. 2154-67.

40. Sheikh, F., et al., *An FHL1-containing complex within the cardiomyocyte sarcomere mediates hypertrophic biomechanical stress responses in mice.* J Clin Invest, 2008. 118(12): p. 3870-80.

41. Linke, W. A., et al., *I-band titin in cardiac muscle is a three-element molecular spring and is critical for maintaining thin filament structure.* J Cell Biol, 1999. 146(3): p. 631-44.

42. LeWinter, M. M., et al., *Cardiac titin: structure, functions and role in disease.* Clin Chim Acta, 2007. 375(1-2): p. 1-9.

The invention claimed is:

1. A method for treating or preventing a cardiac pathology characterized by cardiac hypertrophy comprising administering to an individual in need thereof: a microRNA hsa-miR-665 or a primary transcript of said microRNA hsa-miR-665; or a precursor of said microRNA hsa-miR-665; or a mimic of said microRNA hsa-miR-665; or a DNA coding for said microRNA hsa-miR-665.

2. The method of claim 1, wherein said pathology is selected from the group consisting of a heart failure, a cardiomyopathy, a pathological cardiac hypertrophy, a post-ischemic pathological hypertrophy, a cardiomyopathy of genetic origin, a cardiomyopathy of non-genetic origin, a cardiomyopathy with an hypertrophic phenotype, a myocardial infarction, a cardiomyopathy of ischemic or non-ischemic derivation, a myocardial ischemia and cardiomyopathies of unknown etiology characterized by an increased diastolic dysfunction.

3. The method of claim 1, wherein said cardiac pathology is heart failure with preserved ejection fraction (HFpEF).

4. The method of claim 1, wherein said method comprises preventing a cardiac pathology in an individual at risk of developing cardiac hypertrophy.

5. The method of claim 4, wherein said condition at risk of developing cardiac hypertrophy is selected from the group consisting of chronic hypertension, cardiac valve disease, hereditary cardiomyopathy leading to an hypertrophic phenotype, myocardial infarction, cardiomyocyte loss due to chronic or sudden ischemic damage and cardiomyopathy of ischemic or non-ischemic derivation.

6. The method of claim 1, wherein said microRNA and/or the precursor of said microRNA and/or the mimic of said microRNA and/or the DNA coding for said microRNA and/or the precursor or the mimic of said microRNA, or a combination thereof, is contained in a vector.

7. The method of claim 6, wherein the vector comprises or is a viral vector, wherein optionally the viral vector comprises an adeno-associated vector (AAV) of any capsid serotype, either natural or artificial.

8. The method of claim 1, wherein said microRNA or the primary transcript of said microRNA, or the precursor of said microRNA, and/or the mimic of said microRNA or the DNA coding for said microRNA, primary transcript or precursor or mimic thereof, or a combination thereof, are formulated as or into a pharmaceutical composition and optionally the pharmaceutical composition further comprises at least one pharmaceutically acceptable vehicle or excipient thereof.

9. The method of claim 1, wherein said microRNA, the primary transcript, the precursor or the mimic thereof, is or comprises or is fabricated as an RNA stretch, which is obtained in vitro through cell-free transcription methods, produced synthetically, expressed in a cell upon transfer of an RNA stretch DNA coding sequence, or is introduced or expressed in the cell by administration of a plasmid, or a vector, optionally a viral vector, wherein the plasmid or vector has the RNA stretch DNA coding sequence contained therein.

10. The method of claim 1, wherein said microRNA hsa-miR-665 comprises a sequence as set forth in SEQ ID NO:1.

11. The method of claim 1, wherein said microRNA hsa-miR-665 comprises a sequence as set forth in SEQ ID NO:2.

12. The method of claim 8, wherein the pharmaceutical composition is formulated as a liposome.

13. The method of claim 6, wherein the vector is formulated with or in a liposome.

14. The method of claim 13, wherein said microRNA hsa-miR-665 comprises a sequence as set forth in SEQ ID NO:2.

15. The method of claim 7, wherein the adeno-associated vector (AAV) is an AAV1, AAV2, AAV8 or AAV9 vector.

16. The method of claim 1, wherein said microRNA hsa-miR-665 or the primary transcript of said microRNA hsa-miR-665; or the precursor of said microRNA hsa-miR-665; or the mimic of said microRNA hsa-miR-665; or the DNA coding for said microRNA hsa-miR-665, is administered by intracardiac injection.

17. The method of claim 1, wherein the microRNA hsa-miR-665 or the primary transcript of said microRNA hsa-miR-665; or the precursor of said microRNA hsa-miR-665; or the mimic of said microRNA hsa-miR-665; or the DNA coding for said microRNA hsa-miR-665, is administered by systemic injection.

18. The method of claim 1, comprising administering to an individual in need thereof the microRNA.

19. The method of claim 1, comprising administering to an individual in need thereof the precursor of said microRNA hsa-miR-665.

20. The method of claim 1, comprising administering to an individual in need thereof the DNA coding for said microRNA hsa-miR-665.

* * * * *